Jan. 3 , 1956 E. J. GARDNER Plant Pat. 1,444

LILAC PLANT

Filed May 25, 1953

WITNESS

Addison E. Avery

INVENTOR

EDWARD J. GARDNER, DECEASED.
BY ROBERT L. GARDNER, EXECUTOR

Wheeler, Wheeler & Wheeler
ATTYS.

United States Patent Office

Plant Pat. 1,444
Patented Jan. 3, 1956

1,444

LILAC PLANT

Edward J. Gardner, deceased, late of Horicon, Wis., by Robert L. Gardner, executor, Horicon, Wis., assignor to Robert L. Gardner Application May 25, 1953, Serial No. 357,396

1 Claim. (Cl. 47—60)

This invention relates to a new variety of lilac (*Syringa vulgaris*) plant having large and very compact trusses which are packed with single four and five petaled florets with twisted petals having darker central stripes.

Figures 1, 2:
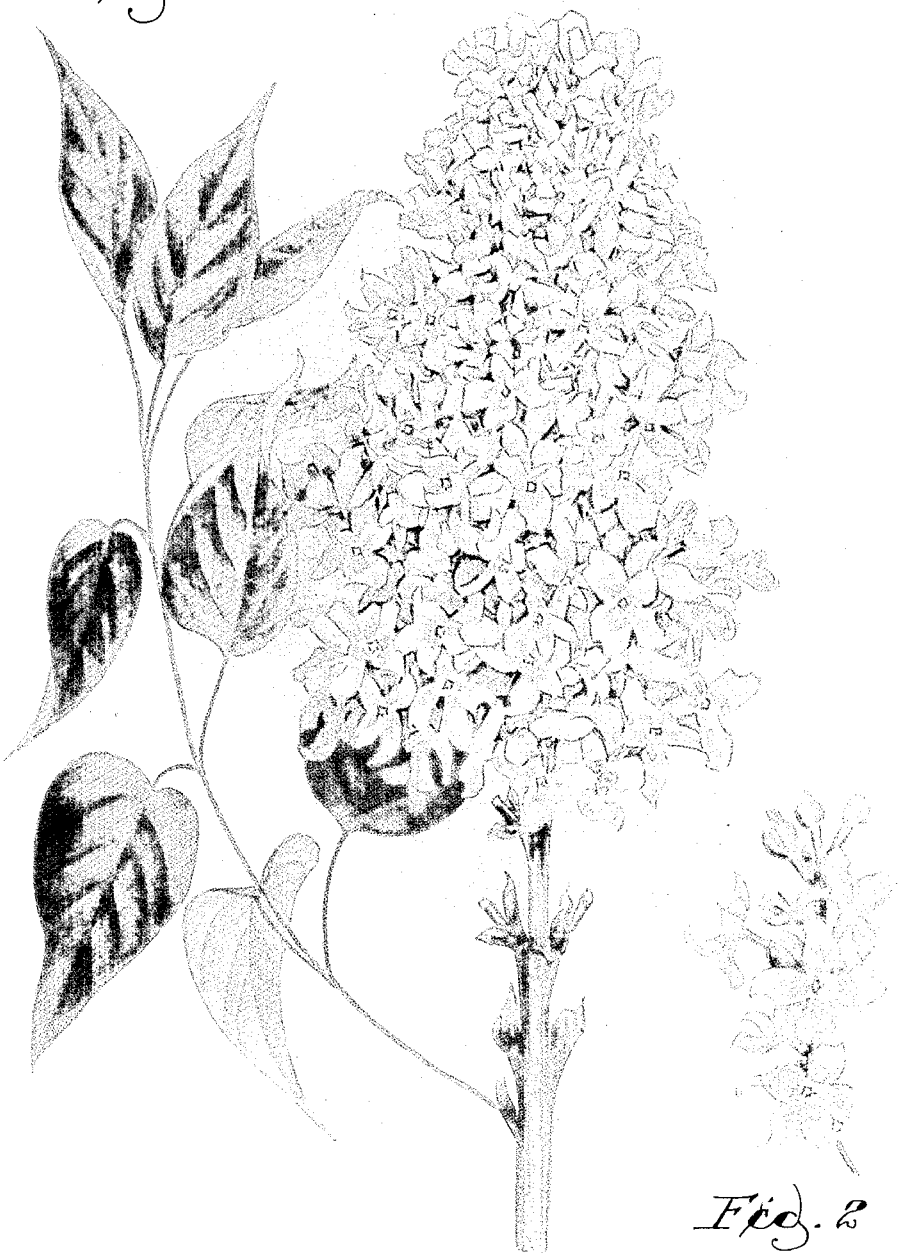
Fig. 1 is a view showing a single panicle of bloom with associated stem and leaves.
Fig. 2 is an enlarged detail view of typical florets in bud and fully open.

The original bush was a seedling of unknown ancestry. It was raised from mixed seed of uncontrolled pollination. The seed was collected from choice nursery varieties. The original bush has been asexually reproduced by rooting cuttings therefrom at Horicon, Wisconsin.

The bush is not markedly different from the bushes of other lilacs except that the leaves are unusually long and pointed. The face of each leaf has a color identified in Maerz and Paul, Dictionary of Color by Plate 22–L–6. The color of the underside or obverse of each leaf is identified in Maerz and Paul, Dictionary of Color by Plate 21–J–70.

The petals of the individual florets are very twisted and extend in various directions from the center of the floret. The calyx is very small. The florets are so packed in the panicle that the panicle has a dense or solid appearance. The color of the small unopened buds is identified in Maerz and Paul, Dictionary of Color by Plate 42–K–7. The edges and ends of the florets have the color identified in Maerz and Paul, Dictionary of Color by Plate 41–D–4. Toward the center of each floret this color deepens. There is no very well defined center stripe, but there is a longitudinally extending area of deeper color identified in Maerz and Paul, Dictionary of Color by Plate 41–D–6.

The pistil of the individual floret is forked and supports two oval stigmas of yellowish color identified in Maerz and Paul, Dictionary of Color by Plate 11–J–1. There are three stamens which are an orange-yellow identified in Maerz and Paul by Plate 10–J–5.

The individual florets quite closely resemble the florets of certain delphinium hybrids which also have petals which are deep reddish purple toward the center, the color gradually becoming paler and approaching a lilac blue at the margins.

The bush bears an exceptionally large number of panicles of bloom and is notable for the fact that in wet weather these exhibit little or no drooping, such as sometimes occurs with hybrid lilacs.

Having thus described some of the outstanding identifying characteristics of the invention, what is claimed is:

A new and distinct variety of lilac plant as described and illustrated and characterized by dense panicles of florets, each having four or five twisted petals which are pale lilac in their background color and have a deeper shade in the center area in each petal.

No references cited.